United States Patent [19]

Suchan et al.

[11] 4,032,627

[45] June 28, 1977

[54] TOOTH WHITENING COSMETIC COMPOSITION

[75] Inventors: Joseph T. Suchan, Freehold; Vincent A. Burell, Bloomsbury, both of N.J.

[73] Assignee: Koh-I-Noor Rapidograph, Inc., Bloomsbury, N.J.

[22] Filed: Aug. 6, 1975

[21] Appl. No.: 602,604

Related U.S. Application Data

[63] Continuation-in-part of Ser. No. 347,102, April 2, 1973, abandoned.

[52] U.S. Cl. .................................. 424/54; 424/49; 106/35
[51] Int. Cl.² ........................................ A61K 7/22
[58] Field of Search ............................ 424/49–54; 106/35 X

[56] References Cited

UNITED STATES PATENTS

| | | | |
|---|---|---|---|
| 636,367 | 11/1899 | Tschirner | 106/35 |
| 1,645,225 | 11/1912 | Welden | 106/35 X |
| 2,413,294 | 12/1946 | Curtis | 106/35 X |
| 2,923,692 | 2/1960 | Ackerman et al. | 424/54 X |
| 3,309,274 | 3/1967 | Brilliant | 106/35 X |

FOREIGN PATENTS OR APPLICATIONS

| | | | |
|---|---|---|---|
| 435,536 | 12/1933 | United Kingdom | 106/35 |
| 1,122,439 | 8/1968 | United Kingdom | 424/81 |

*Primary Examiner*—Lewis Gotts
*Assistant Examiner*—Cary Owens
*Attorney, Agent, or Firm*—David H. Semmes

[57] ABSTRACT

A tooth whitening cosmetic composition of the type applied temporarily to the dry tooth surface and removable by solvent. The cosmetic composition is characterized by its lustrous white appearance, extended wearing time, thicker viscosity and ease of removal with solvent.

8 Claims, No Drawings

TOOTH WHITENING COSMETIC COMPOSITION

CROSS-REFERENCES TO RELATED APPLICATION

This application is a continuation-in-part of Ser. No. 347,102, filed Apr. 2, 1973, and now abandoned.

BACKGROUND OF THE INVENTION

1. Field of the Invention

Cosmetics, particularly non-toxic tooth whitening compositions applied to the teeth as a beauty aid. The cosmetics industry and its researchists have devoted large scale attention to hair treatment, low calorie or dieting foods, skin treatment, beautification of eyes, finger and toe nails. More recently inventors have directed themselves to the beautification of teeth, recognizing the fact that the middle-age tooth has a discolored or devitalized appearance which can be improved.

2. Description of the Prior Art

ACKERMAN, et al. U.S. Pat. No. 2,923,692;
PICKEL U.S. Pat. No. 3,223,588;
GLASS, et al. U.S. Pat. No. 2,980,655;
MATSUMURA, et al. U.S. Pat. No. 2,975,102.

SUMMARY OF THE INVENTION

According to the present invention, a lustrous and relatively long-wearing cosmetic composition is applied directly to the dried tooth surface. The wearing time of the composition being directly related to its application upon a dry surface, its curing upon the dry surface and its insulation from the abrasive action of eating.

The composition is readily removable by a solvent such as 50% ethyl alcohol and 50% water combined with a green food coloring and peppermint flavoring.

DESCRIPTION OF THE PREFERRED EMBODIMENTS

The tooth whitener composition provides a more youthful appearance to the male or female. In short, it is for both sexes and can be used on natural teeth and-/or dentures. Of course, if any dental pathology is present, a dentist should be consulted.

It is an accepted fact that, in the young, teeth are brighter and more lustrous, while as one grows older, teeth darken. Bridges and dentures also darken with age. Other fields of beauty care have reached a high level of commerical attention such as:

a. the areas of hair with shampoos, conditioners, rinses, wigs, etc.;
b. the body with its various dimensions as to size and weight which has promoted special diets, spas, low caloric foods, reducing devices, etc.;
c. the treatment of the skin with the use of creams and various types of makeup;
d. the beautifying of the eyes with eyeliners, eye shadows, mascara, false lashes, etc.;
e. the beautifying of finger and toe nails with various polishers and conditioners.

It is fundamental that, for greater beauty, a uniformly bright, lustrous set of teeth is as important as beautiful hair, the trimness of shapliness of the body, or the soft unwrinkled skin. Both male and female look best when all these features are combined with a bright lustrous set of teeth.

The present tooth whitener composition is non-toxic as researched and reaffirmed by competent Toxicology Test by the Biotoxicology Laboratories, Merchantville, N.J. The toxicology of tooth whitener composition was assayed for ingestion. Since tooth whitener is not ingested per se, its toxic effects are reduced considerably as noted or compared in the toxicology study.

It is known that approximately 10–15% of the population over 30 years of age have discolored or devitalized teeth, whether they are one's own natural teeth or dentures. Of course, natural teeth to be whitened must be sound. Otherwise, dental care and not beauty care is required. The appeal for tooth whitener may thus depend to a major degree on effective marketing.

Prior to the application of tooth whitener, normal dental hygiene is recommended; namely, the brushing of the teeth, the use of an irrigating device such as that known as the Water Pik, and the use of dental floss. The application of tooth whitener is simply as long as the outer surfaces of the teeth to be coated are dry. It is a fundamental truth that it is a most difficult task to apply any coating to a moist surface. As with any technique, practice leads to perfection. The application of tooth whitener is similar to the application of nail polish insofar as one tooth is coated at a time. Most persons require coating only the upper eight or ten front teeth, The lower teeth are seldom exposed in speaking or smiling. However, it is very easy to coat the lower teeth should this be desired as for entertainers, public speakers, etc.

The wearing time of tooth whitener is directly related to:

a. its application on a dry surface;
b. the longer the dry time, the longer the wearing time;
c. the abrasive action of the food eaten after its application.

The lower teeth having been coated, will flake more than the upper teeth since the upper teeth hold while the lower teeth provide the cutting action. In other words, the damage to the teeth whitener coating during eating is dependent on what and how one eats. The abrasive action of foods such as spareribs, corn on the cob, dry toasted breads, pretzels, etc., will wear away the tooth whitener faster than soft foods. With the proper application of tooth whitener and careful eating, tooth whitener will be unaffected grossly until it is removed by the brushing of the teeth and/or use of a special solvent.

Seventy-five percent or more of the tooth whitener has been removed by normal brushing of the teeth. The remainder or residue of tooth whitener can be removed by the use of a suggested solvent, such as equal parts of ethyl alcohol and water, flavored with peppermint and perhaps, colored green with food dye, which is antiseptic to the gums and teeth. During the day, when removal of the tooth whitener is not desired, the use of mouth washes or rinses can be substituted for the brushing of the teeth. At the end of the day, as noted above, normal dental hygiene procedures are recommended. Should the tooth whitener begin to wear during dinner, one has the option of removing it completely or retouching the flaked areas. It is common practice to retouch lipstick after eating. In short, tooth whitener is applied like nail polish but may wear like lipstick.

It is strongly suggested that tooth whitener is contraindicated if any dental pathology is present, such caries, peridonal conditions, etc. For dental pathology present, consult your dentist.

The advantage of tooth whitener is that it affords a uniform, bright lustrous coating of sound of non-carious discolored or devitalized teeth. With brighter and more natural teeth, tooth whitener can help achieve a more youthful appearance, a greater degree of beauty for the female, and a greater degree of handsomeness for the male.

Application of tooth whitener — emulates dental technique. Coat upper eight or ten central teeth.

1. Shake bottle vigorously.
2. Place a piece of dried Expando Plastic Strip between the upper lip and gum slightly beyond the area to be covered.
3. Dry thoroughly the upper teeth desired for the application with tooth whitener with a smaller piece of dried Expando Plastic Strip under the tongue to absorb saliva. In the dental office, a suction device is used.
4. Shake bottle again.
5. Ensure that the bristles of the brush in the bottle are saturated with tooth whitener.
6. It is wiser to start applying tooth whitener to the upper cuspid teeth and then doing the incisor teeth in sequence. The incisor teeth will tolerate less error in coating. It is important to coat only one tooth at a time. Rebrushing over the same tooth creates a streaking effect. Usually, a second coating is not required.
7. After all desired areas are coated, allow a minimum of five minutes drying time if no eating is anticipated. The longer the drying time, the longer the wearing time. It is estimated that ten to fifteen minutes of drying time is ideal. Good wearing time is dependent on drying time of the tooth whitener. It is suggested that while waiting for the drying time to elapse, other chores such a the application of one's deodorant, the brushing of hair, dressing, etc., be performed. Thus drying time will not appear to be excessive. In short, good wearing time is most desirable.
8. After the proper drying time has occurred, remove both pieces of the Expando Plastic material and moisten the coated teeth with one's tongue.
9. Both pieces of Expando Plastic material can be washed with soap and water, rinsed, dried thoroughly (with mild heat as from as electric bulb), and reused.

Suggested formulations include:
Formula I:

| | |
|---|---|
| Zinc oxide | .42% |
| H₂O | 4.54% |
| Concentrated Ammonium Hydroxide | 1.08% |
| Ammonium Carbonate | 0.76% |
| Carboset Resin 514-A | 27.19% |
| Ethanol Alcohol | 60.08% |
| Methocel HG | 1.39% |
| Chromalite Black | 0.16% |
| D and C Red 6 | 0.16% |
| Titanium Dioxide | 4.20% |

Procedure

Zinc Oxide, Water, Concentrated Ammonium Hydroxide and Ammonium Carbonate are used to form a complex system to cross link the Carboset Resin. Free Ammonium should be expelled before the product is used. Carboset Resin 514-A is used as film former. Methocel HG is also a film forming and pigment suspending agent. Ethanol is used as a solvent. Titanium Dioxide, Chromalite Black, which is the common name for Bismuth Oxychloride and Carbon Black, and D and C Red 6 are all of which are known and listed coloring additives of pigment agents in the formulation.

Formula II:

Part A

| | |
|---|---|
| Zinc oxide | 6.31% |
| H₂O | 65.31% |
| Concentrated NH₄OH | 17.11% |
| Ammonium Carbonate | 11.26% |

Part B

| | |
|---|---|
| Carboset 514-A | 39.40% |
| Part A | 9.85% |
| Ethanol | 49.26% |
| Methocel HG | 1.48% |

Part C

| | |
|---|---|
| Ethanol | 10.01% |
| Part B | 70.07% |
| Titanium Dioxide | 4.00% |
| Yellow Food Dye Solution | 15.02% |
| Iron Oxide Black | .15% |
| Methyl Paraben | .25% |
| Propyl Parben | .25% |
| Peppermint | .25% |

Yellow B-3 Solution

| | |
|---|---|
| Ethanol | 99.600% |
| Yellow Food Dye (FD & C yellow No. 6) | .400% |

Procedure

Part A — Zinc Oxide is added to water and dissolved: Ammonium carbonate is then added and stirred until it is completely dissolved. Finally the concentrated Ammonium Hydroxide is added. The solution at this point should be completely clear.

Part B — Carboset 514-A resin and ethanol are mixed together in a blender. When it is apparent that Carboset 514-A is completely dispersed in the ethanol, Methocel HG is then added. This mixture is then blended until it is smooth and free of lumps.

Part C — A and B are added together and mixed until homogenous. The pigments are then added and blended together and the whole mixture is put through a homogenizer.

Metholcel HG is a trade name for methylcellulose, known as hydroxypropyl methylcellulose manufactured by Dow Chemical Company of Midland, Mich. Carboset Resin 514-A is a tradename for an acrylic film forming resin manfactured by B. F. Goodrich Chemical Co., of Cleveland, Ohio.

It should be noted that while the Carboset 514 resin, supplied as 70% solids in isopropyl alcohol in the 514-A form is illustrated as a preferred film-forming agent in the above-noted preferred embodiments, the use of other known mucilaginous bodying agents are contemplated for use within this invention. Specifically, the above-incorporated patent to Ackerman, U.S. Pat. No. 2,923,692, illustrates the well known equivalence between synthetic cross-linked polymers and such conventional natural bodying agents as, for example, gum tragacanth, as film forming agents. It is considered that, for the film forming purposes herein, any such type of film forming agent is equivalent to that particularly illustrated acrylic-acrylate co-polymer solution which has been identified as Carboset 514. Any other such mucilaginous film agent composition having a resin, or natural material of the types noted in Ackerman when dissolved as 70 percent solids in isopropyl alcohol would be efficacious for the limited purposes intended herein of being a binder and film forming medium. This particular proprietary product has no more generic description which is in the public domain. As is well-known, Carboset 514-A is an acrylic - acrylate copolymer resin supplied as 70 percent solids in isopropyl alcohol. However, the fixed and definite meaning and therefore continuing efficacy of Carboset 514-A for the purposes herein intended is assured by reference to the external standards of the Food and Drug Administration. The FDA has registered the Carboset 514-A resin as R. 0011772 in the C.T.F.A.

Manifestly, variations in ingredients as well as their method of mixing may be employed without departing from the spirit of the invention.

I claim:

1. A non-toxic tooth whitening composition consisting essentially of the following component solutions:
    A. a first component comprising zinc oxide, approximately 6.3 percent; ammonium hydroxide, approximately 17.1 percent; ammonium carbonate, approximately 11.3 percent; with the balance water;
    B. a second component comprising said first component as approximately 9.85 percent; a 70% solution of a mucilaginous bodying material, capable of functioning as a film forming agent, in isopropyl alcohol approximately 39.4 percent; methyl cellulose approximately 1.5 percent; with the balance ethanol; said second component comprising 70 percent of the total composition;
    C. a third component comprising; said second component as approximately 70 percent; a non-toxic yellow food dye solution, approximately 15 percent; titanium dioxide, approximately 4 percent; with the balance ethanol.

2. A tooth whitening cosmetic composition as in claim 1, wherein said yellow dye solution is approximately 0.4% FD & C yellow No. 6 and the remainder ethanol.

3. A tooth whitening cosmetic composition as in claim 1, wherein said 70% solution of a film forming agent in isopropyl alcohol is Carboset 514-A.

4. A tooth whitening cosmetic composition consisting essentially of:
    A. a 70% solution of a mucilaginous bodying agent, capable of functioning as a film forming agent, in isopropyl alcohol, approximately 27.2 percent;
    B. water, approximately 4.5 percent;
    C. titanium dioxide, approximately 4.2 percent;
    D. methyl cellulose, approximately 1.4 percent;
    E. ammonium hydroxide, approximately 1.1 percent;
    F. ammonium carbonate, approximately 0.76 percent;
    G. zinc oxide, approximately 0.42 percent;
    H. non-toxic pigment agents and food coloring dyes, approximately 0.32 percent;
    I. ethanol, the balance percentage.

5. Method for making a tooth whitening cosmetic composition consisting essentially of:
    A. dissolving in water a solution of approximately 6.3 percent zinc oxide and approximately 17.1 percent concentrated ammonium hydroxide and 11.3 percent ammonium carbonate;
    B. mixing a second solution comprising approximately 9.85 percent solution A, approximately 39.4 percent of a 70% solution of a mucilaginous bodying material, capable of functioning as a film forming agent, in isopropyl alcohol, approximately 49.2 percent ethanol, and approximately 1.5 percent methyl cellulose;
    C. mixing together the solutions of subparagraph A and B until homogenous; and
    D. making a third solution comprising approximately 70 percent solution B, together with non-toxic coloring pigments and a nontoxic yellow food dye solution suspended in ethanol, then homogenizing.

6. Method for making a tooth whitening cosmetic composition as in claim 5, wherein said coloring pigments are titanium dioxide and said yellow dye solution is approximately 0.4% FD & C No. 6 and the remainder ethanol.

7. A tooth whitening cosmetic composition as in claim 4, wherein said 70% solution a film forming agent in isopropyl alcohol is Carboset 514-A.

8. A tooth whitening cosmetic composition as in claim 5, wherein said 70% solution of a film forming agent in isopropyl alcohol is Carboset 514-A.

* * * * *